(12) United States Patent
Yoo et al.

(10) Patent No.: US 8,517,947 B2
(45) Date of Patent: Aug. 27, 2013

(54) ULTRASOUND SYSTEM AND METHOD FOR PERFORMING VESSEL LABELING

(75) Inventors: Jae Heung Yoo, Seoul (KR); Dong Gyu Hyun, Seoul (KR); Kwang Hee Lee, Seoul (KR)

(73) Assignee: Medison Co., Ltd., Kangwon-Do (KR)

( * ) Notice: Subject to any disclaimer, the term of this patent is extended or adjusted under 35 U.S.C. 154(b) by 479 days.

(21) Appl. No.: 12/852,363

(22) Filed: Aug. 6, 2010

(65) Prior Publication Data

US 2011/0034807 A1 Feb. 10, 2011

(30) Foreign Application Priority Data

Aug. 10, 2009 (KR) .......................... 10-2009-0073365

(51) Int. Cl.
*A61B 8/00* (2006.01)
(52) U.S. Cl.
USPC .......................................... 600/443; 600/437
(58) Field of Classification Search
None
See application file for complete search history.

(56) References Cited

U.S. PATENT DOCUMENTS

| | | | |
|---|---|---|---|
| 7,925,064 B2 | 4/2011 | Cloutier et al. | |
| 2008/0119734 A1 | 5/2008 | Pruvot et al. | |
| 2008/0137927 A1 | 6/2008 | Altmann et al. | |
| 2009/0003675 A1* | 1/2009 | Moreau-Gobard | 382/131 |

FOREIGN PATENT DOCUMENTS

| | | |
|---|---|---|
| JP | 07-178086 | 7/1995 |
| JP | 07-178086 A | 7/1995 |
| JP | 2002-269539 A | 9/2002 |
| JP | 2007-512862 A | 5/2007 |
| KR | 10-2008-0053224 A | 6/2008 |

OTHER PUBLICATIONS

Korean Office Action issued in Korean Patent Application No. KR 10-2009-0073365 dated Sep. 28, 2011.
Kirbas et al., "Vessel Extraction Techniques and Algorithms: A Survey," Proceedings of the Third IEEE Symposium on BioInformatics and BioEngineering, 8 pages (2003).
Stefancik et al., "Highly Automated Segmentation of Arterial and Venous Trees from Three-Dimensional Magnetic Resonance Angiography (MRA)," The International Journal of Cardiovascular Imaging 17: 37-47 (2001).
Extended European Search Report for EP 10170229.8-2319, 8 pages, dated Oct. 26, 2010.

* cited by examiner

*Primary Examiner* — Long V. Le
*Assistant Examiner* — Faizah Ahmed
(74) *Attorney, Agent, or Firm* — McDermott Will & Emery LLP

(57) ABSTRACT

There are disclosed embodiments for an ultrasound system for performing vessel labeling. The ultrasound system comprises: an ultrasound data acquisition unit configured to transmit an ultrasound signal to a target object including vessels, receive an ultrasound echo signal reflected from the target object and form ultrasound data corresponding to the target object; a volume data forming unit configured to form volume data based on the ultrasound data; and a processor configured to form a 3-dimensional ultrasound image based on the volume data, perform vessel segmentation on the 3-dimensional ultrasound image to provide at least one segmented image including at least one segmented vessel, detect at least one vessel junction from the at least one segmented vessel and perform vessel labeling on the at least one segmented image based on the detected at least one vessel junction.

4 Claims, 6 Drawing Sheets

ULTRASOUND SYSTEM AND METHOD FOR PERFORMING VESSEL LABELING

CROSS-REFERENCE TO RELATED APPLICATIONS

The present application claims priority from Korean Patent Application No. 10-2009-0073365, filed on Aug. 10, 2009, the entire subject matter of which is incorporated herein by reference.

TECHNICAL FIELD

The present disclosure generally relates to ultrasound systems, and more particularly to an ultrasound system and method for automatically performing vessel labeling.

BACKGROUND

An ultrasound system has been extensively used for acquiring internal information of a target object due to its non-invasive and non-destructive nature. Since the ultrasound system may provide a high resolution image without any surgical treatment, it has proven to be very helpful in the medical profession.

Generally, the ultrasound system may provide 3-dimensional ultrasound images including clinical information such as spatial information and anatomical information, which 2-dimensional ultrasound images do not include. The ultrasound system may operate to transmit an ultrasound signal to a target object, receive the ultrasound signal reflected from the target object (i.e., ultrasound echo signal) and acquire ultrasound data. The ultrasound system may form volume data by using the acquired ultrasound data and provide a 3-dimensional image through rendering of the formed volume data.

Also, the ultrasound system may perform segmentation on the 3-dimensional ultrasound image and extract an object of interest from the 3-dimensional ultrasound image. However, if a structure of vessel is complicated after performing segmentation, then it is difficult to recognize a specific vessel among many vessels as well as to locate vessel connection points (or junctions).

SUMMARY

There are disclosed embodiments of an ultrasound system and a method adapted to perform segmentation of vessel and automatically labeling on the vessel. In one embodiment, by way of non-limiting example, the ultrasound system comprises: an ultrasound data acquisition unit configured to transmit an ultrasound signal to a target object including vessels, receive an ultrasound echo signal reflected from the target object and form ultrasound data corresponding to the target object; a volume data forming unit configured to form volume data based on the ultrasound data; and a processor configured to form a 3-dimensional ultrasound image based on the volume data, perform vessel segmentation on the 3-dimensional ultrasound image to provide at least one segmented image including at least one segmented vessel, detect at least one vessel junction from the at least one segmented vessel and perform vessel labeling on the at least one segmented image based on the detected at least one vessel junction.

In another embodiment, a method of performing segmentation of vessels, comprises: a) transmitting an ultrasound signal to a target object including vessels and receiving an ultrasound echo signal reflected from the target object to thereby form ultrasound data corresponding to the target object; b) forming volume data based on the ultrasound data; c) forming a 3-dimensional ultrasound image based on the volume data; d) performing vessel segmentation on the 3-dimensional ultrasound image to provide at least one segmented image including at least one segmented vessel; e) detecting at least one vessel junction from the at least one segmented vessel; and f) performing vessel labeling on the at least one segmented image based on the detected at least one vessel junction.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

DETAILED DESCRIPTION

A detailed description may be provided with reference to the accompanying drawings.

Figure 1:
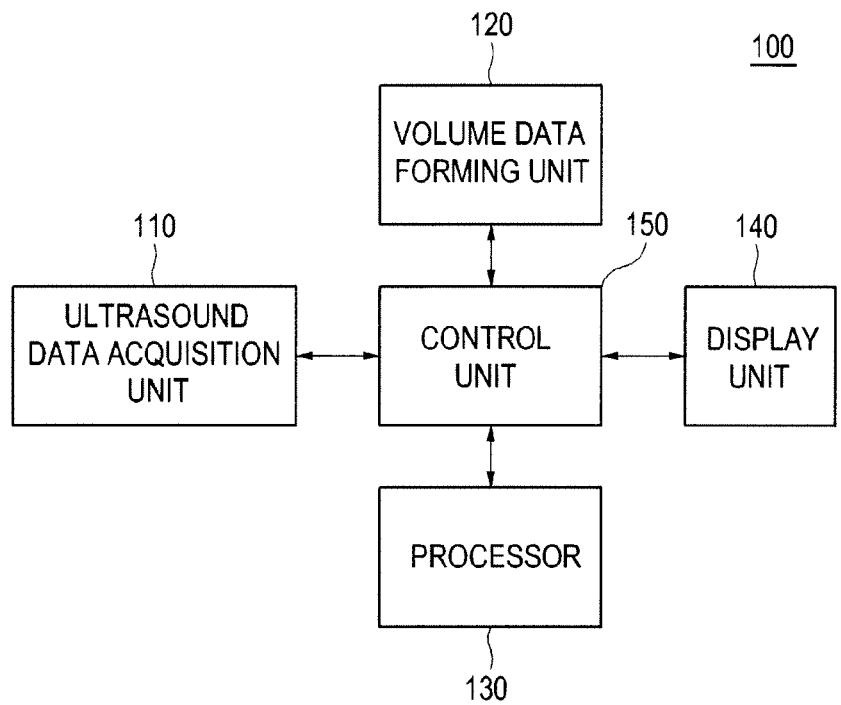
FIG. 1 is a block diagram showing an illustrative embodiment of an ultrasound system.

FIG. 1 is a block diagram showing an illustrative embodiment of an ultrasound system 100 which embodies the methods of the present invention. The ultrasound system 100 comprises an ultrasound data acquisition unit 110, a volume data forming unit 120, a processor 130, a display unit 140 and a control unit 150.

The ultrasound data acquisition unit 110 may be operable to transmit an ultrasound signal to a target object, and receive the ultrasound signal (i.e., ultrasound echo signal) reflected from the target object to thereby acquire ultrasound data.

Figure 2:
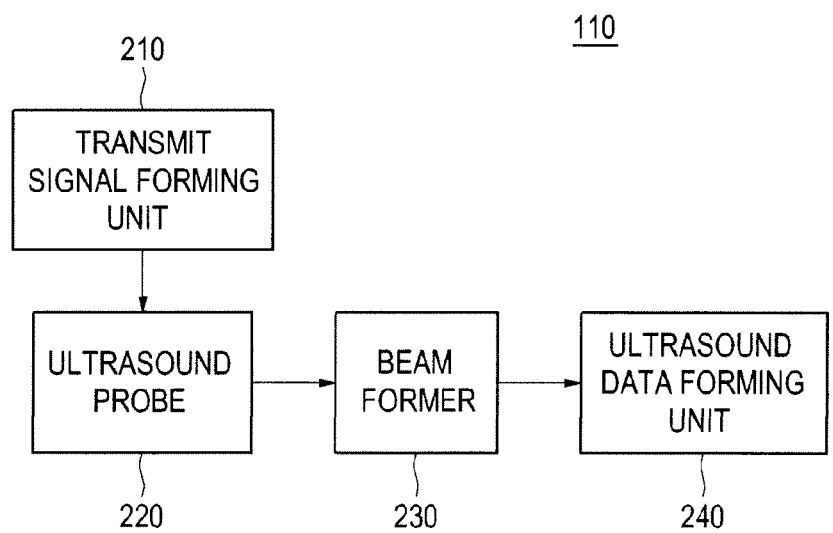
FIG. 2 is a block diagram showing an illustrative embodiment of an ultrasound data acquisition unit.

FIG. 2 is a block diagram showing an illustrative embodiment of the ultrasound data acquisition unit 110. The ultrasound data acquisition unit 110 may include a transmit signal forming unit 210, an ultrasound probe 220 including a plurality of transducer elements (not shown), a beam former 230 and an ultrasound data forming unit 240.

The transmit signal forming unit 210 may be operable to form a transmit signal to be applied to each of the transducer elements of the ultrasound probe 220. By way of a non-limiting example, the positions and focusing points of the transducer elements may be considered in forming the transmit signal. In one embodiment, the transmit signal may include a transmit signal for acquiring a plurality of frames of the target object.

The ultrasound probe 220 may operate to convert the transmit signal provided by the transmit signal forming unit 210 into an ultrasound signal and transmit it to the target object.

The ultrasound probe 220 may further operate to receive the ultrasound echo signal reflected from the target object and form a receive signal.

The beam former 230 may be configured to form a digital signal through analog-to-digital conversion of the receive signal provided by the ultrasound probe 220. The beam former 230 may operate to perform receive-focusing upon the digital signal in consideration of the positions and focusing points of the transducer elements, and form a receive-focused signal thereby.

The ultrasound data forming unit 240 may be configured to form ultrasound data of the target object using the receive-focused signal provided by the beam former 230. In one embodiment, the ultrasound data may comprise RF (radio frequency) data and IQ (in-phase/quadrature) data.

Referring back to FIG. 1, the volume data forming unit 120 may operate to form volume data by using the ultrasound data provided by the ultrasound acquisition unit 110. The volume data may comprise a plurality of frames and a plurality of voxels having brightness values.

The processor 130 may operate to form a 3-dimensional ultrasound image including vessels in the target object by using the volume data provided by the volume data forming unit 120, and perform segmentation of the vessels and vessel labeling by using the 3-dimensional ultrasound image.

Figure 3:
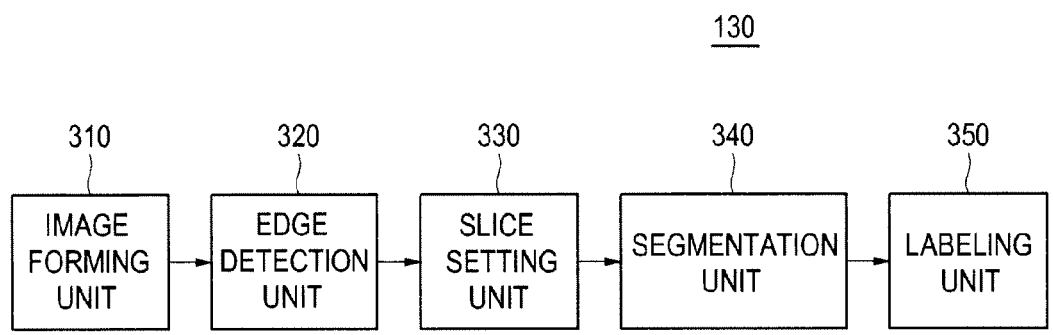
FIG. 3 is a block diagram showing an illustrative embodiment of a processor.

FIG. 3 is a block diagram showing an illustrative embodiment of the processor 130. The processor 130 comprises an image forming unit 310, an edge detection unit 320, a slice setting unit 330, a segmentation unit 340 and a labeling unit 350.

The image forming unit 310 may operate to form the 3-dimensional ultrasound image through rendering of the volume data provided by the volume data foaming unit 120. In one embodiment, the rendering may comprise ray-casting rendering, surface rendering, etc.

The edge detection unit 320 may operate to detect vessel edges through performing edge detection on the 3-dimensional ultrasound image provided by the image forming unit 310. In one embodiment, the vessel edges may be detected by using an edge mask such as a Sobel mask, a Prewitt mask, a Robert mask, a Canny mask, etc. Also, the vessel edges may be detected from the difference of eigen values by using a structure tensor.

Figure 4:
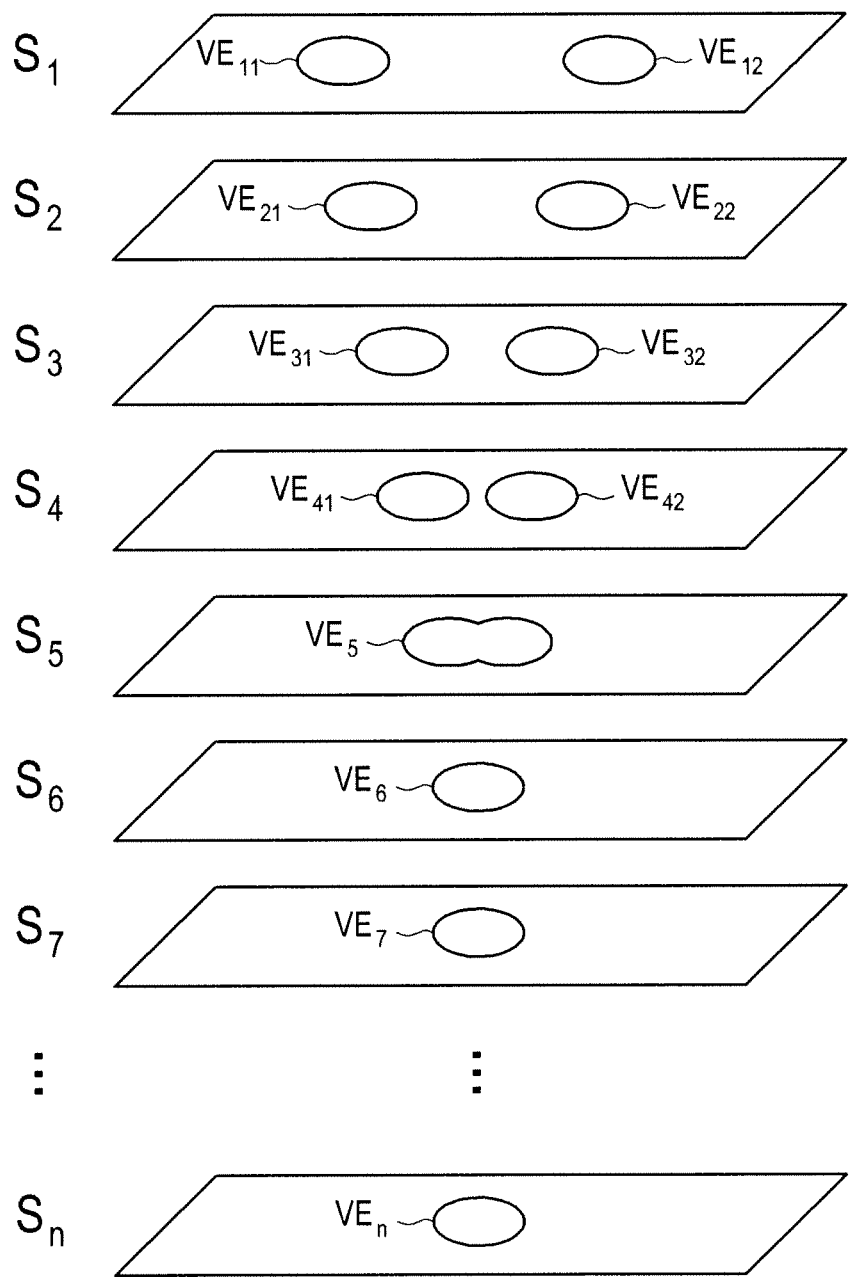
FIG. 4 is a schematic diagram showing an example of a plurality of slices and vessel edges.

The slice setting unit 330 may operate to set a plurality of slices $S_0$ to $S_n$ on the 3-dimensional ultrasound image in which the vessel edges were detected, as illustrated in FIG. 4. In one embodiment, the plurality of slices may comprise slices corresponding to the plurality of frames.

The segmentation unit 340 may be configured to perform segmentation of the vessels based on a degree of registration between the respective vessels on the adjacent slices. In one embodiment, the segmentation unit 340 may operate to compare the location of vessels on adjacent slices by using the vessel edges and perform segmentation of the vessels. An illustrative operation of the segmentation unit 340 will be described with reference to FIGS. 4 to 6.

The segmentation unit 340 may operate to analyze a first slice $S_1$ and detect vessel edges $VE_{11}$, $VE_{12}$ on the first slice $S_1$.

Figure 5:
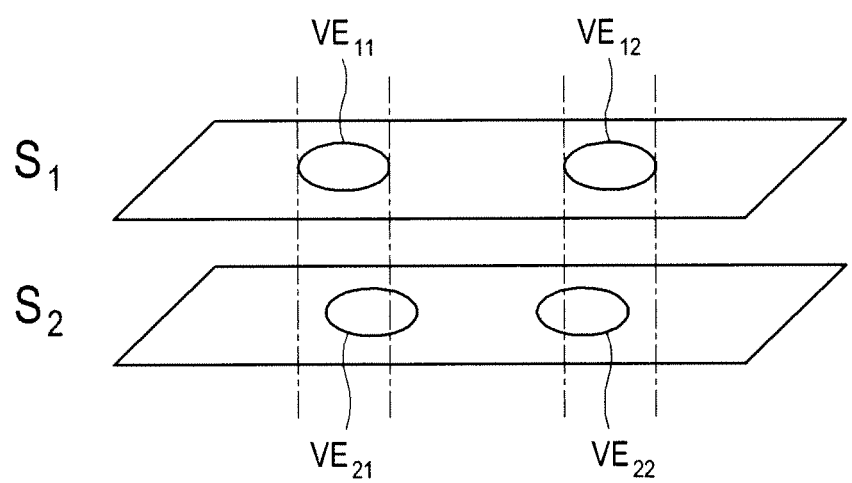
FIG. 5 is a schematic diagram showing an example of location difference between vessel edges on adjacent slices.

The segmentation unit 340 may operate to analyze a second slice $S_2$ and detect vessel edges $VE_{21}$, $VE_{22}$ on the second slice $S_2$. The segmentation unit 340 may operate to detect location difference between the vessel edges on the adjacent slices (i.e., the first slice $S_1$ and the second slice $S_2$), as illustrated in FIG. 5. Specifically, the segmentation unit 340 may operate to detect the location difference between the vessel edge $VE_{11}$ of the first slice $S_1$ and the vessel edge $VE_{21}$ of the second slice $S_2$, as well as the location difference between the vessel edge $VE_{11}$ of the first slice $S_1$ and the vessel edge $VE_{22}$ of the second slice $S_2$. Further, the segmentation unit 340 may operate to detect the location difference between the vessel edge $VE_{12}$ of the first slice $S_1$ and the vessel edge $VE_{21}$ of the second slice $S_2$, as well as the location difference between the vessel edge $VE_{12}$ of the first slice $S_1$ and the vessel edge $VE_{22}$ of the second slice $S_2$. When the location difference between the vessel edge $VE_{11}$ of the first slice $S_1$ and the vessel edge $VE_{21}$ of the second slice $S_2$ and the location difference between the vessel edge $VE_{12}$ of the first slice $S_1$ and the vessel edge $VE_{22}$ of the second slice $S_2$ are equal to or less than a predetermined threshold, and the location difference between the vessel edge $VE_{11}$ of the first slice $S_1$ and the vessel edge $VE_{22}$ of the second slice $S_2$ and the location difference between the vessel edge $VE_{12}$ of the first slice $S_1$ and the vessel edge $VE_{21}$ of the second slice $S_2$ are more than the predetermined threshold, the segmentation unit 340 may connect the vessel edge $VE_{21}$ of the second slice $S_2$ with the vessel edge $VE_{11}$ of the first slice $S_1$, and connect the vessel edge $VE_{22}$ of the second slice $S_2$ with the vessel edge $VE_{12}$ of the first slice $S_1$. The segmentation unit 340 may perform the same operation with respect to a third slice $S_3$ and a fourth slice $S_4$, as described above.

The segmentation unit 340 may operate to analyze a fifth slice $S_5$ and detect a vessel edge $VE_5$ on the fifth slice $S_5$. The segmentation unit 340 may operate to detect the location difference between the vessel edges on the adjacent slices (i.e., the fourth slice $S_4$ and the fifth slice $S_5$). When the location difference between the vessel edge $VE_{41}$ of the fourth slice $S_4$ and the vessel edge $VE_5$ of the fifth slice $S_5$ and the location difference between the vessel edge $VE_{42}$ of the fourth slice $S_4$ and the vessel edge $VE_5$ of the fifth slice $S_5$ are equal to or less than the predetermined threshold, the segmentation unit 340 may connect the vessel edge $VE_5$ of the fifth slice $S_5$ with the vessel edges $VE_{41}$, $VE_{42}$ of the fourth slice $S_4$.

The segmentation unit 340 may operate to analyze a sixth slice $S_6$ and detect a vessel edge $VE_6$ on the sixth slice $S_6$. The segmentation unit 340 may operate to detect the location difference between the vessel edges on the adjacent slices (i.e., the fifth slice $S_5$ and the sixth slice $S_6$). When the location difference between the vessel edge $VE_5$ of the fifth slice $S_5$ and the vessel edge $VE_6$ of the sixth slice $S_6$ are equal to or less than the predetermined threshold, the segmentation unit 340 may connect the vessel edge $VE_6$ of the sixth slice $S_6$ with the vessel edge $VE_5$ of the fifth slice $S_5$.

Figure 6:
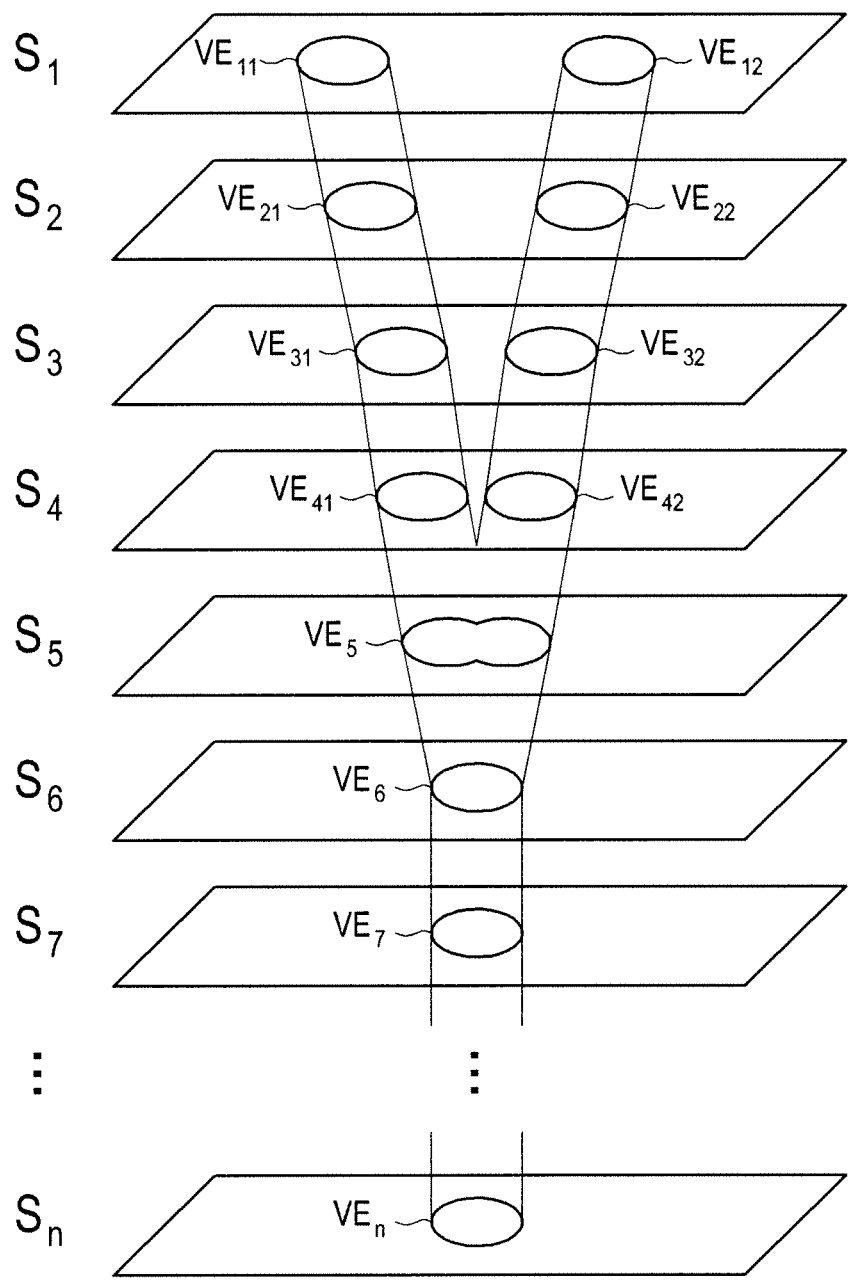
FIG. 6 is a schematic diagram showing an example of segmentation of vessel.

The segmentation unit 340 may perform the same operation with respect to a seventh slice $S_7$ to an nth slice $S_n$, as described above in order to perform segmentation of the vessels, as illustrated in FIG. 6.

Although in the aforementioned embodiment, segmentation of vessels is performed by setting a plurality of slices on the 3-dimensional ultrasound image and calculating location differences between the edges of the vessels on each adjacent pair of the slices, the present invention is certainly not limited thereto. In another embodiment, segmentation of a vessel may be performed using another well-known method of segmentation.

Figure 7:
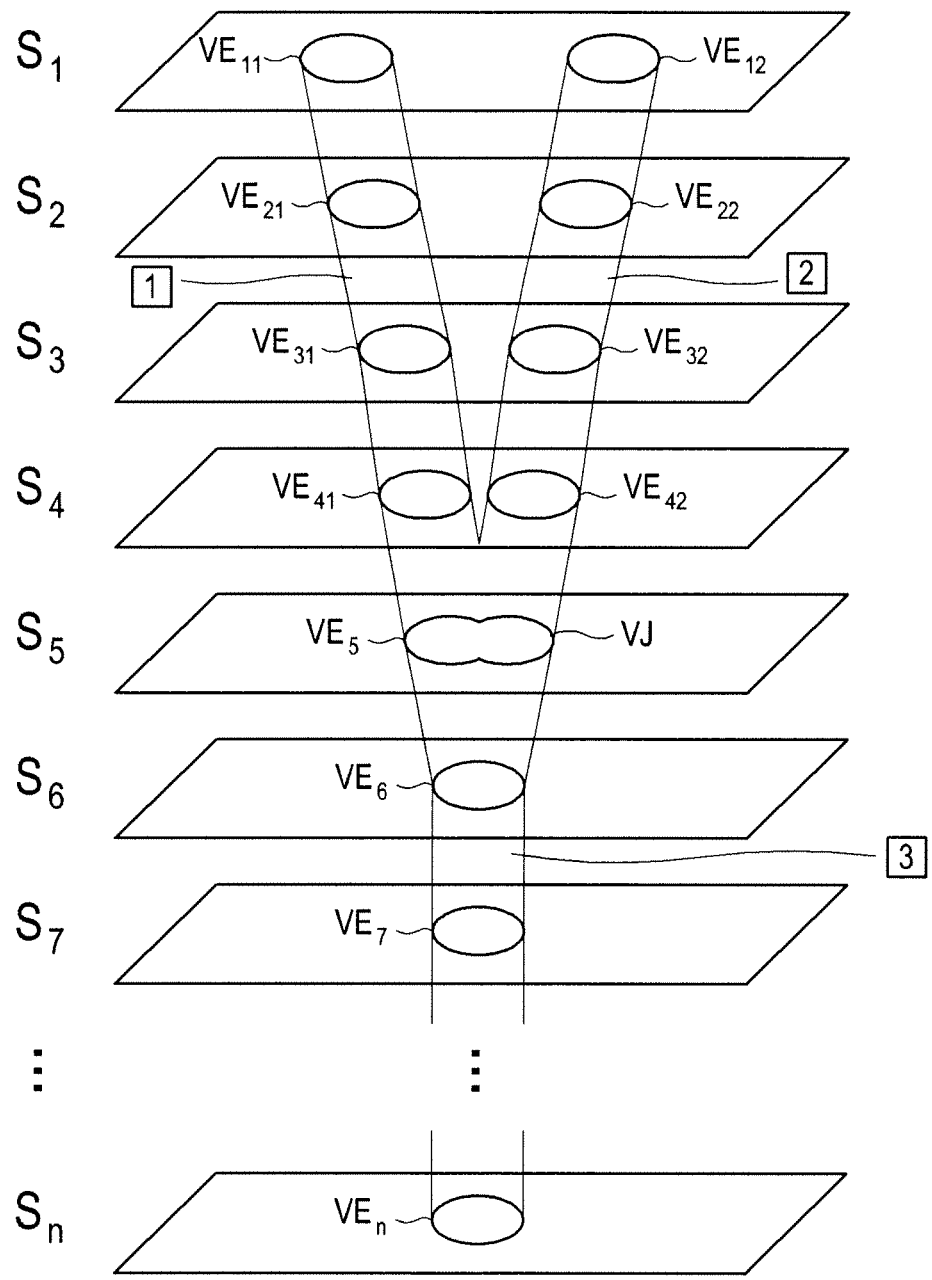
FIG. 7 is a schematic diagram showing an example of labeled vessels.

The labeling unit 350 may operate to detect vessel junctions using edges of vessels on a respective plurality of slices after segmentation of vessels and perform vessel labeling based on the detected vessel junctions. In one embodiment, labeling unit 350 may operate to detect a vessel junction VJ analyzing a respective plurality of slices, as illustrated in FIG. 7. The vessel junction VJ may comprise a junction where one vessel diverges to at least two vessels or at least two vessels join and merge to one vessel. The labeling unit 350 may operate to perform vessel labeling based on the vessel junction VJ. Although in FIG. 7, vessel labeling is performed based on the vessel junction VJ with number, the present invention is certainly not limited thereto. In another embodiment, vessel labeling may be performed with at least one of number, text and color.

Referring back to FIG. 1, the display unit 140 may operate to display the 3-dimensional ultrasound image formed by the processor. The display unit 140 may further operate to display the 3-dimensional ultrasound image on which the processor 130 performed segmentation of the vessels. In one embodiment, the display unit 140 may include a liquid crystal display (LCD), a cathode ray tube (CRT) or any other device capable of displaying an image.

The control unit 150 may operate to control acquisition of the ultrasound data, and formation of the volume data and the 3-dimensional ultrasound image. The control unit 150 may further operate to control image processing of the 3-dimensional ultrasound image (i.e., segmentation of the vessels and vessel labeling).

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements within the scope of the disclosure, the drawings and the appended claims. In addition to variations and modifications in the component parts and/or arrangements, alternative uses will also be apparent to those skilled in the art.

What is claimed is:

1. An ultrasound system, comprising:
   an ultrasound data acquisition unit configured to transmit an ultrasound signal to a target object including vessels, receive an ultrasound echo signal reflected from the target object and form ultrasound data corresponding to the target object;
   a volume data forming unit configured to form volume data based on the ultrasound data; and
   a processor configured to form a 3-dimensional ultrasound image based on the volume data, perform edge detection on the 3-dimensional ultrasound image to detect edges of the vessels, set a plurality of slices on the edge-detected 3-dimensional ultrasound image, calculate differences in location between edges of the vessels on each adjacent pair of the slices, compare the calculated location differences with a predetermined threshold and connect edges based on a result of the comparison, perform vessel segmentation of the vessels based on the connected edges to form segmented vessels, detect at least one vessel junction from the segmented vessels and perform vessel labeling on the segmented vessels based on the detected at least one vessel junction.

2. The ultrasound system of claim 1, wherein the processor is configured to perform the vessel labeling on the segmented vessels with at least one of a number, text and color.

3. A method of performing segmentation of vessels, comprising steps of:
   transmitting an ultrasound signal to a target object including vessels and receiving an ultrasound echo signal reflected from the target object to thereby form ultrasound data corresponding to the target object;
   forming volume data based on the ultrasound data;
   forming a 3-dimensional ultrasound image based on the volume data;
   performing edge detection on the 3-dimensional ultrasound image to detect edges of the vessels;
   setting a plurality of slices on the edge-detected 3-dimensional ultrasound image;
   calculating differences in location between edges of the vessels on each adjacent pair of the slices;
   comparing the calculated location differences with a predetermined threshold and connecting edges based on a result of the comparison;
   performing vessel segmentation of the vessels based on the connected edges to form segmented vessels;
   detecting at least one vessel junction from the segmented vessels; and
   performing vessel labeling on the segmented vessels based on the detected at least one vessel junction.

4. The method of claim 3, wherein the step of performing vessel labeling, comprises the step of:
   performing the vessel labeling on the segmented vessels with at least one of number, text and color.

\* \* \* \* \*